United States Patent [19]

Yamazaki

[11] 4,398,327

[45] Aug. 16, 1983

[54] PLEDGET LOADING APPARATUS

[75] Inventor: Sakuzo Yamazaki, Kiryu, Japan

[73] Assignee: Sankin Engineering Company Limited, Kiryu, Japan

[21] Appl. No.: 220,250

[22] Filed: Dec. 24, 1980

[30] Foreign Application Priority Data

Dec. 29, 1979 [JP] Japan .................................. 54-172347

[51] Int. Cl.³ .............................................. B23P 21/00
[52] U.S. Cl. .................................. 29/33 R; 29/564.8; 29/782; 604/1
[58] Field of Search ................ 29/564.6, 564.8, 33 R, 29/432, 789, 782, 797, 798, 811; 128/269, 274

[56] References Cited

U.S. PATENT DOCUMENTS

| | | | |
|---|---|---|---|
| 3,018,778 | 1/1962 | Brilliant | 128/269 |
| 3,255,494 | 6/1966 | Block et al. | 128/269 X |
| 3,443,562 | 5/1969 | Gustafson | 128/269 |
| 3,542,025 | 11/1970 | Gustafson | 128/269 |
| 4,017,955 | 4/1977 | Hermanson | 29/564.8 |
| 4,339,868 | 7/1982 | Mazzer | 29/782 X |

Primary Examiner—William R. Briggs
Attorney, Agent, or Firm—Martin Smolowitz

[57] ABSTRACT

A pledget loading apparatus for automatically applying a cut segment of a flocculent material such as absorbent cotton to the needle of an elongated needle instrument such as a dental probe needle instrument. The instrument is inserted into an instrument receiver unit to be loaded with such a pledget on the needle and is automatically conveyed into a position ready to be removed from the apparatus. A continuous length of flocculent material is stepwise supplied and cut into segments in an area suitable for being applied to the needle of the instrument.

9 Claims, 16 Drawing Figures

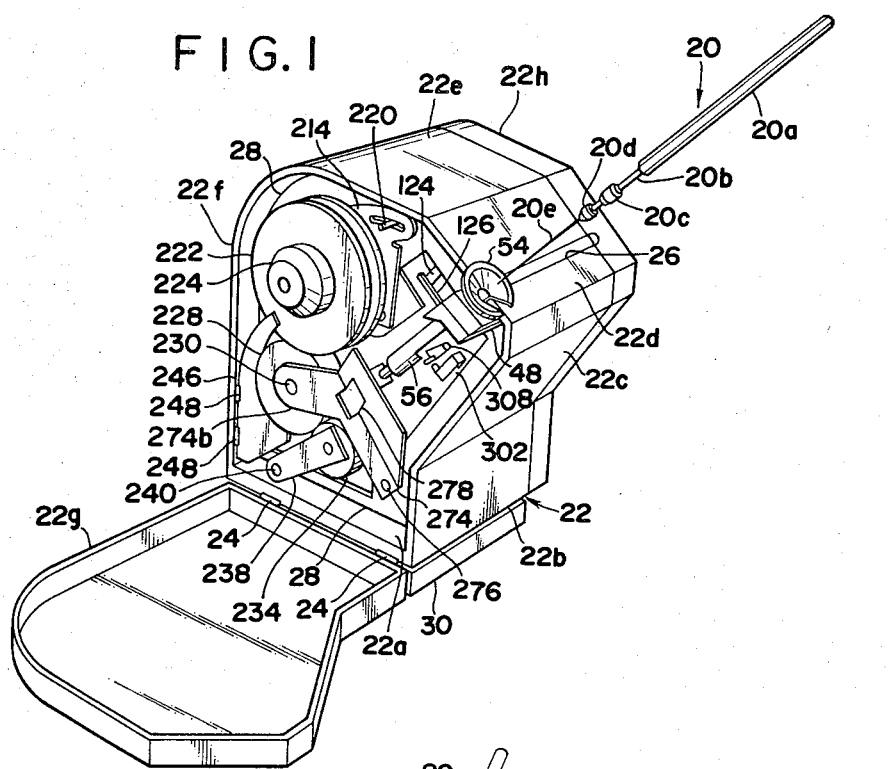
FIG. 1
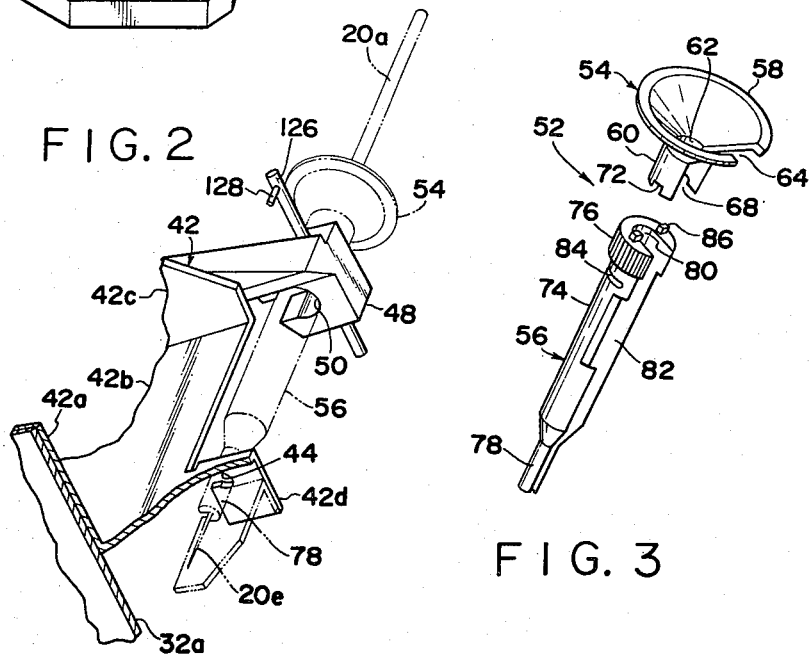
FIG. 2
FIG. 3

PLEDGET LOADING APPARATUS

FIELD OF THE INVENTION

The present invention relates to an apparatus for automatically applying a cut segment of flocculent material to an elongated needle instrument having a needle and, particularly, to a pledget loading apparatus in which a pledget or any segment of a flocculent material such as absorbent cotton is to be automatically applied to the probe of, typically, a dental explorer or probe needle instrument.

BACKGROUND OF THE INVENTION

In detecting, examining or cleaning dental cavities or anaethizing tooth roots in dental cavities, a dental explorer or probe needle instrument is used with a piece of absorbent cotton applied to the pointed needle of the instrument. Such piece of cotton is usually formed between finger tips and applied by fingers to the needle of the instrument prior to the use of the instrument. A time-consuming effort is required each time a pledget of such form is applied to the instrument and skilled techniques must be employed to the pledget and apply the pledget to the needle of the instrument. The present invention contemplates provision of a pledget loading apparatus useful for automatically applying a pledget to the needle of a dental probe instrument or another kind of elongated instrument having a needle.

SUMMARY OF THE INVENTION

In accordance with the present invention, there is provided an apparatus comprising, in combination, an instrument receiver unit for receiving therein at least an axial portion of a needle instrument in such a manner that the needle of the instrument axially projects out of the receiver unit, the instrument receiver unit having an axial bore extending and being laterally open throughout the length of the unit, thrust-out means operative to thrust the needle instrument laterally out of the axial bore in the instrument receiver unit into a predetermined first position laterally adjacent the receiver unit, transfer means operative to convey the needle instrument from the first position to a predetermined second position remote from the first position, supply means for storing a continuous length of a flocculent material thereon and feeding a leading end portion of the continuous length of flocculent material to a predetermined delivery area into which the needle of the instrument extends axially when the instrument is received in said instrument receiver unit, and cutting means operative to cut the leading end portion into a segment in the delivery area.

BRIEF DESCRIPTION OF THE DRAWINGS

The features and advantages of a pledget loading apparatus according to the present invention will be more clearly appreciated from the following description taken in conjunction with the accompanying drawings, in which:

FIG. 1 is a perspective view showing a preferred embodiment of the pledget loading apparatus according to the present invention;

FIG. 2 is a fragmentary and partially cut-away perspective view showing portions of a internal support structure of the pledget loading apparatus embodying the present invention as illustrated in FIG. 1;

FIG. 3 is an exploded perspective view showing an instrument receiver unit forming part of the pledget loading apparatus embodying the present invention;

DESCRIPTION OF THE EMBODIMENT

Figure 4:
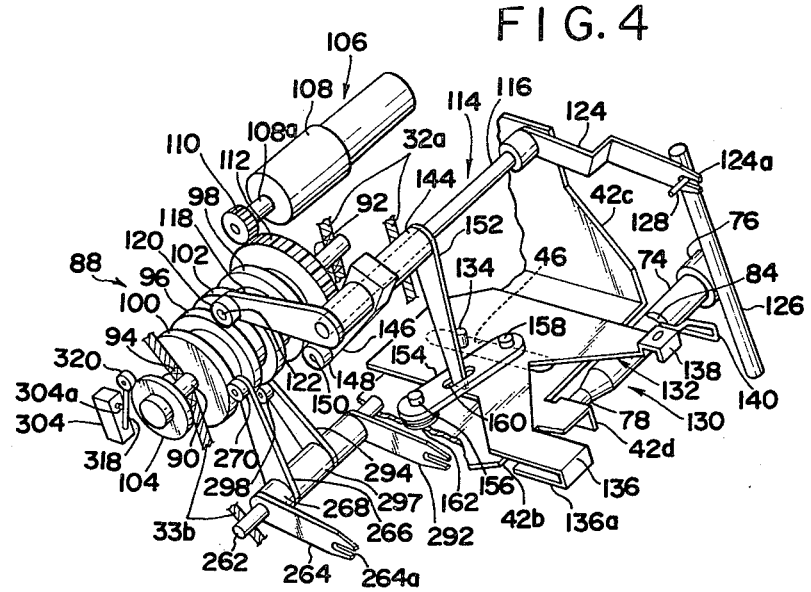
FIG. 4 is a perspective view showing a cam mechanism, a pledget supply mechanism and a thrust-out mechanism forming part of the embodiment of the pledget loading apparatus according to the present invention.

In the following description, it will be assumed, by way of example, that the pledget loading apparatus embodying the present invention is to be used for applying a pledget or a piece of absorbent cotton to the pointed needle of a dental explorer. As is well known in the art, a dental explorer is a probe needle instrument used for the purpose of detecting, examining or cleaning dental cavities or anaesthetizing tooth roots in dental cavities.

In the accompanying drawings, particularly in FIG. 1 thereof, such a probe needle instrument is designated generally by reference numeral 20 and is shown comprising an elongated grip rod portion 20a having, for example, a hexagonal cross section, a shank portion 20b axially projecting forward from the grip rod portion 20a, a barrel-shaped neck portion 20c securely or detachably fitted to the shank portion 20b, a needle holder element 20d removably fitted to a foremost end portion of the neck portion 20c, and a pointed needle 20e connected to and axially projecting forward from the needle holder element 20d. Such a configuration of the probe needle instrument 20 is, however, merely illustrative of various types of probe needle instruments presently in use in the art of dental surgery and, thus, it should be borne in mind that the apparatus according to the present invention is operable for applying a piece of cotton or any other flocculent material to the pointed end portion of a needle forming part of any surgical or hygenical instrument or implement.

Referring concurrently to FIGS. 1 to 5 of the drawings, the pledget loading apparatus embodying the present invention comprises a generally box-shaped external housing structure 22. As illustrated in FIG. 1, the external housing structure 22 has a horizontal bottom wall portion 22a, a vertical lower front wall portion 22b upstanding from the front end of the bottom wall portion 22a, an inclined lower front wall portion 22c inclined forwardly and upwardly from the upper end of the vertical lower front wall portion 22b, an inclined upper front wall portion 22d inclined rearwardly and still upwardly from the upper end of the inclined upper front wall portion 22c, a horizontal top wall portion 22e extending rearwardly from the upper and rearward end of the inclined upper front wall portion 22d, and a vertical rear wall portion 22f upstanding from the rear end of the bottom wall portion 22a and gradually curved upwardly and forwardly into the top wall portion 22e.

The external housing structure 22 further has a pair of side wall members consisting of left and right side wall members 22g and 22h each configured conformingly to the vertical section defined by the above mentioned wall portions 22a to 22e. The side wall members 22g and 22h are hingedly connected along their lower ends to the side ends of the bottom wall portion 22a of the housing structure 22 as indicated at 24 in conjunction with the left side wall member 22g in FIG. 1. Each of the side wall members 22g and 22h is thus pivotally movable about an axis parallel with each side end of the bottom wall portion 22a of the housing structure 20 and is held in an upright position closing the housing structure 22 when the pledge loading apparatus as shown is in use.

Figure 5:
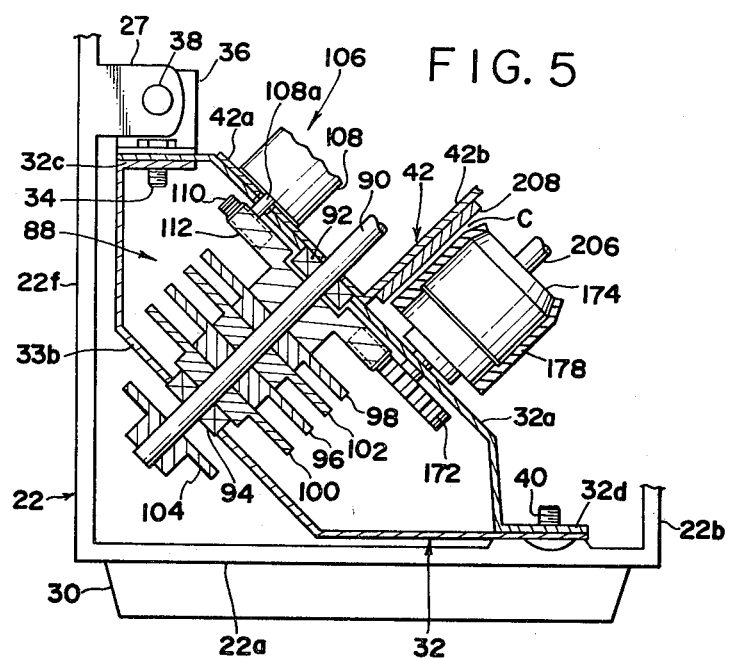
FIG. 5 is a fragmentary vertical sectional view showing the cam mechanism, drive means, and part of a transfer mechanism of the embodiment of the pledget loading apparatus embodying the present invention.

The inclined upper front wall portion 22d of the housing structure 22 is formed with a horizontally elongated slot 26 having a predetermined length. On the other hand, the vertical rear wall portion 22f of the housing structure 22 has a pair of internal lugs projecting forwardly from the inner face of the wall portion 22f as shown in FIG. 5 in which one of the lugs is shown at 27. Though not shown in the drawings, the two lugs 27 thus formed on the vertical rear wall portion 22f of the housing structure 22 are spaced apart in parallel from each other in a lateral direction of the housing structure 22.

The housing structure 22 further includes a pair of internal side members one of which is seen partially in FIG. 1 and designated by reference numeral 28. The internal side members 28 are also spaced apart in parallel from each other in a lateral direction of the housing structure 22 and are fixedly located adjacent the lateral ends of the internal space defined by the wall portions 22a to 22f of the housing structure 22. Furthermore, the housing structure 22 is positioned on a bottom base member 30 secured to the bottom wall portion 22a of the housing structure 22 as shown in FIG. 1.

The external housing structure 22 constructed as above described has a "major frontal plane" which is herein defined as a plane parallel with the outer face of the inclined upper front wall portion 22d of the housing structure 22. As will have be understood from the description regarding the wall portion 22d, the major frontal plane of the housing structure 22 is inclined upwardly in a rearward direction of the housing structure 22 from a horizontal plane.

The external housing structure 22 has mounted therein an internal support structure which is designated generally by reference numeral 32 in FIG. 5. The internal support structure 32 has inclined front and rear wall portions 32a and 33b which are substantially parallel with the above mentioned major frontal plane of the housing structure 22. The inclined front and rear wall portions 32a and 33b are spaced apart from each other in a direction perpendicular to the major frontal plane and have an open end space formed therebetween. The internal support structure 32 further has a horizontal top wall portion 32c extending rearwardly from the upper end of the inclined front wall portion 32a, and a horizontal bottom wall portion 32d extending forwardly from the lower end of the inclined rear wall portion 33b. The internal support structure 32 as a whole is securely connected to the external housing structure 22 by bolts or screws 34 fastening the above mentioned top wall portion 32c to the lugs 27 of the rear wall portion 22f of the housing structure. By means of brackets 36 and pins or studs 38 and further by bolts or screws 40 the above mentioned bottom wall portion 32d of the support structure 32 is fastened to the bottom wall portion 22a of the housing structure 20 as shown in FIG. 5.

The internal support structure 32 further includes an upper support member 42 having an inclined rear wall portion 42a securely attached to the outer or front face of the inclined front wall portion 32a of the support structure 32, and an inclined intermediate wall portion 42b which is bent substantially perpendicularly from the lower end of the inclined rear wall portion 42a (see FIGS. 2 and 5). As shown in FIG. 2, the upper support member 42 further has an inclined front wall portion 42c which is forwardly and upwardly spaced apart substantially in parallel from the inclined rear wall portion 42a. The inclined front wall portion 42c of the upper support member 42 is located in close vicinity to and substantially parallel with the inner face of the inclined upper front wall portion 22d of the external housing structure 22 and has a lower end located slightly above the elongated slot 26 in the wall portion 22d.

As shown in FIGS. 2 and 4 of the drawings, the upper support member 42 further has a lug portion 42d which is downwardly bent substantially in a perpendicular direction from the intermediate wall portion 42b of the support member 42 and which is thus substantially parallel with the major frontal plane of the external housing structure 22. The lug portion 42d of the support member 42 is rearwardly spaced apart for a predetermined distance from the inner face of the inclined upper front wall portion 22d of the housing structure 22 and is located close to the inner face of the left side wall member 22g of the housing structure 22. The lug portion 42d is formed with a generally lying U-shaped slot 44 having a circular portion which is laterally open in a rightward direction, viz., away from the inner face of the above mentioned side wall member 22g of the housing structure 22. The lug portion 42d of the support member 42 is, furthermore, forwardly spaced apart a certain distance from the inclined front wall portion 32a of the internal support structure 32 as will be seen from FIG. 2. As indicated partially by dotted lines in FIG. 4, the intermediate wall portion 42b of the upper support member 42 is formed with a horizontally elongated slot 46 having a predetermined length.

The internal support structure 32 further includes a front supporting block 48 which is fixedly attached to the outer or front face of the inclined front wall portion 42c of the above described support member 42 and which has a lateral end portion forwardly spaced apart, in face-to-face relationship, to the lug portion 42d of the support member 42 as shown in FIG. 2. The front supporting block 48 is positioned between the left side wall member 22g of the housing structure 20 and the left internal side member 28. It is formed with a generally U-shaped slot 50 having a cylindrical portion which is laterally open rightwardly, viz., away from the inner face of the left side wall member 22g of the housing structure 22 as will be seen from FIG. 1. The cylindrical portion of the U-shaped slot 50 has a central axis substantially aligned with the central axis of the circular portion of the U-shaped slot 44 in the lug portion 42d of the upper support member 42, in a direction substantially normal to the major frontal plane of the housing structure 22. The slot 44 in the lug portion 42d and the slot 50 in the supporting block 48 are further substantially aligned with a left end portion of the elongated slot 26 in the inclined upper front wall portion 22d of the external housing structure 22. The left internal side member 28 is positioned laterally and inwardly of the lug portion 42d and the above mentioned end portion of the supporting block 48. It is formed with an opening which is open to the space extending between these slots 44 and 50.

The pledge loading apparatus embodying the present invention further comprises an instrument receiver unit 52 for receiving therein a probe needle instrument when the instrument is to be loaded with a pledget. As illustrated in FIG. 3 of the drawings, the instrument receiver unit 52 is of a two-piece construction consisting of a generally funnel-shaped front socket member 54 and a generally cylindrical sleeve member 56. The socket member 54 in turn comprises a trumpet-shaped inlet portion 58 and a generally cylindrical extension 60 axially projecting from the reduced rear axial end of the inlet portion 58. The trumpet-shaped inlet portion 58 is formed with a frusto-conical concavity which is enlarged and open forwardly of the inlet portion 58, while the cylindrical extension 60 is formed with an axial bore 62 axially extending rearwardly from the reduced rear end of the frusto-conical concavity in the inlet portion 58 and open at the rear axial end of the extension 60. The trumpet-shaped inlet portion 58 is further formed with a radial groove 64 extending throughout the radial length of the inlet portion 58 and radially inwardly merging into the axial bore 62 in the cylindrical extension 60. The axial bore 62 in the cylindrical extension 60 has a generally U-shaped cross section which is open as at 68 throughout the axial length of the extension 60 in a radial direction coincident with the radial direction in which the radial groove 64 extends and merges into the bore 62. Thus, the radial groove 64 in the trumpet-shaped inlet portion 58 and the radially open axial bore 62 form, in combination, a continuous groove which is radially open throughout the axial length of the socket member 54. The cylindrical extension 60 of the socket member 54 is further formed with a pair of axial recesses 72 which are rearwardly open endwise of the extension 60 and which are located in substantially diametrically opposed relationship to each other across the center axis of the extension 60.

On the other hand, the cylindrical sleeve member 56 of the instrument receiver unit 52 has an elongated stem portion 74, an externally toothed foremost spur gear portion 76 formed at the rear of the stem portion 74, and a reduced rear end portion 78 axially projecting rearwardly from the stem portion 74. The sleeve member 56 is formed with an axial bore 80 extending throughout its axial length, viz., axially through the stem portion 74, spur gear portion 76 and reduced rear end portion 78. The axial bore 80 also has a generally U-shaped cross section which is radially open as at 82 throughout the length of the sleeve member 56. The spur gear portion 76 of the sleeve member 56 is, thus, radially void through a foremost end portion of the radially open axial groove 80. The stem portion 74 axially intervening between the spur gear portion 76 and the reduced rear end portion 78 of the sleeve member 56 is formed with a quadrant slot 84 which is located axially in the neighborhood of the spur gear portion 76. The quadrant slot 84 extends circumferentially in the stem portion 74 through the central angle of approximately 90 degrees about the central axis of the sleeve member 56 between circumferentially opposite ends one of which is located substantially in diametrically opposed relationship to the radially open end of the axial groove 80 in the sleeve member 56 and the other of which is located substantially at right angles to the radially open end of the groove 80 as will be better seen from FIG. 7.

The sleeve member 56 has a pair of projections 86 axially projecting forwardly from the generally C-shaped front end face of the spur gear portion 76. The axial projections 86 of the sleeve member 56 are located substantially in diametrically opposed relationship to each other, across the central axis of the sleeve member 56 and are adapted to be respectively received in the above mentioned axial recesses 72 in the cylindrical extension 60 of the socket member 54. The socket member 54 and the sleeve member 56 can thus be assembled together by mating engagement between the axial recesses 72 in the socket member 54 and the axial projections 86. When the socket member 54 and the sleeve member 56 are connected together to complete the instrument receiver unit 52 in this manner, the axial bore 62 and the radial groove 64 in the socket member 54 and the axial bore 80 in the sleeve member 56, are radially open in identical directions. The axial grooves 62 and 80 and the radial groove 64 in the instrument receiver unit 52 form, in combination, a continuous groove which is radially open throughout the axial length of the instrument receiver unit 52. The axial bores 62 and 80 in the instrument receiver unit 52 are so shaped and sized as to receive therein the previously described probe needle instrument 20 with the grip rod portion 20a of the instrument partially projecting outwardly frm the frusto-conical concavity in the trumpet-shaped inlet portion 58 of the socket member 54. The stem and reduced rear end portions 74 and 78, in particular, of the sleeve member 56, are internally shaped so that the probe needle instrument 20 can reach a predetermined axial position with respect to the instrument receiver unit 52 when the probe needle instrument 20 is inserted into the receiver unit 52 as far as the instrument is permitted to move axially through the axial bores 62 and 80 in the receiver unit 52, as will be seen from FIG. 16.

The instrument receiver unit 52 constructed as hereinbefore described is detachably fitted to the upper support member 42 and the front supporting block 48 with the sleeve member 56 axially inserted through the U-shaped slot 50 in the front supporting block 48 and the U-shaped slot 44 in the lug portion 42d of the upper support member 42, as indicated by dots-and-dash lines in FIG. 2. The instrument receiver unit 52 thus held in position by the upper support member 42 and the front supporting block 48 has the spur portion 76 of its sleeve member 56, positioned in front of the supporting block 48 and the reduced rear end portion 78 of the sleeve member 56, axially projecting rearwardly from the lug portion 42d of the support plate 42. The quadrant slot 84 in the stem portion 74 of the sleeve member 56 is located at the rear of the plane on which the inner face of the inclined front wall portion 42c of the support member 42 lies, as will be seen from FIG. 4. Furthermore, the stem portion 74 and the reduced rear end portion 78 of the sleeve member 56 of the instrument receiver unit 52 are slidably received in the U-shaped slots 50 and 44, respectively. Therefore, the instrument receiver unit 52 as a whole, is turnable about the central axis thereof, between a latched or inoperative angular position, having the axial bores 62 and 80 radially open downwardly and an unlatched or operative angular position having the axial bores 62 and 80 radially open rightwardly of the housing structure 20, viz., radially aligned with the radially open end portions of the respective slots 44 and 50 in the support member 42 and the supporting block 48. When the instrument receiver unit 52 is held in the latched or inoperative angular position, the axial bore 80 in the sleeve member 56 of the receiver unit 52 is isolated from the radially open end portions of the slots 44 and 50. At the same time, the quadrant slot 84 in the stem portion 74 of the sleeve member 56 has one of its circumferential ends located at or in the vicinity of the top of the cross section of the stem portion 74 of the sleeve member 56 and the other of the circumferential ends located at the rightmost end of the cross section of the stem portion 74, viz., radially directed in the direction in which each of the respective slots 44 and 50 in the support plate 42 and the supporting block 48 is radially open. When, on the other hand, the instrument receiver unit 52 is held in the unlatched or operative angular position thereof, about the central axis of the unit 52, the axial bore 80 in the stem portion 74 of the sleeve member 56 is radially open and directly contiguous to the radially open end portions of the respective slots 44 and 50 in the support member 42 and the supporting block 48. At the same time, the quadrant slot 84 in the stem portion 74 of the sleeve member 56, has one of its circumferential ends located at or in the vicinity of the top of the cross section of the stem portion 74 and the other of the circumferential ends located at the leftmost end of the cross section of the stem portion 74, viz., radially directed opposite to the direction in which each of the respective slots 44 and 50 in the support member 42 and the supporting block 48 is radially open, as will be seen from FIG. 7. Thus, the quadrant slot 84 in the stem portion 74 of the sleeve member 56 is open in such a manner, as to allow an access therein from the lefthand side of the stem portion 74 when the instrument receiver unit 52 is in the unlatched or operative angular position about the center axis thereof. When the instrument receiver unit 52 is in the latched or inoperative angular position about the central axis thereof, the quadrant slot 84 in the stem portion 74 of the sleeve member 56 is open in such a manner as to be inaccessible therein from the lefthand side of the stem portion 74. When the instrument receiver unit 52 is in the unlatched or operative angular position thereof, the radial groove 64 in the funnel-shaped socket member 54 of the receiver unit 52, radially extends in a direction substantially parallel to the direction in which the elongated slot 26 in the inclined upper front wall portion 22d of the external housing 22 extends longitudinally.

The pledget loading apparatus embodying the present invention further comprises various operational elements, members and units accommodated within the housing structure 22. These operational elements, members and units are actuated and operated under the control of a cam mechanism which is illustrated principally in FIGS. 4 and 5 of the drawings and which is designated generally by reference numeral 88.

As shown in FIGS. 4 and 5, the cam mechanism 88 comprises a cam shaft 90 which is journalled in bearings 92 and 94 retained in openings formed in the inclined front and rear wall portions 32a and 32b, respectively, of the internal support structure 32. The cam shaft 90 axially extends in a direction substantially normal to the major frontal plane of the housing structure 22 and is thus rotatable about is center axis with respect to the support structure 32. The cam shaft 90 has fixedly mounted thereon a parallel combination of first, second, third and fourth motion control cam members 96, 98, 100 and 102, which are positioned between the inclined front and rear wall portions 32a and 32b of the support structure 32 and which are rotatable as a single unit with the cam shaft 90 about the central axis of the cam shaft 90. The cam shaft 90 axially projects rearwardly from the inclined rear wall portion 32b of the support structure 32 and further has a switch control cam member 104 fixedly mounted on a projecting rear end portion of the shaft 90.

The cam shaft 90 thus carrying the four cam members 96, 98, 100, 102 and 104 thereon is driven to rotate about the center axis thereof by drive means 106 also illustrated principally in FIGS. 4 and 5 of the drawings.

The drive means 106 comprises an electric motor 108 supported by the inclined rear and front wall portion 42a and 42c of the support member 42. The motor 108 has an output shaft 108a extending substantially in parallel with the cam shaft 90 and axially projecting rearwardly frm the inclined front wall portion 32a of the support structure 32 through an opening formed in the wall portion 32a. The output shaft 108a of the motor 108 has fixedly mounted on its end portion a gear 110 which is in constant mesh with a gear 112 fixedly and coaxially mounted on the cam shaft 90 and positioned inside the inclined front wall portion 32a of the support structure 32.

The pledget loading apparatus embodying the present invention further comprises an unlatching mechanism which is best seen in FIG. 4 of the drawings and which is designated generally by reference numeral 114. The unlatching mechanism 114 is adapted to operate the above described instrument receiver unit 52 to turn between the latched and unlatched or inoperative and operative angular positions thereof under the control of the first cam member 96 included in the cam mechanism 88.

As shown in FIG. 4, the unlatching mechanism 114 comprises a shaft 116 substantially parallel with the cam shaft 90 and rotatable about its central axis on the front inclined wall portion 32a of the support structure 32 and the inclined front wall portion 42c of the upper support member 42. The shaft 116 axially projects rearwardly from the inclined front wall, portion 32a of the support structure 32 and has securely mounted on its rear end portion a first arm member 118 which is rotatable with the shaft 116 about the central axis of the shaft. The first arm member 118 has on its leading end portion, a cam follower roller 120 acting by means of a pivot pin 122 having a central axis substantially parallel with the shaft 116 and accordingly with the cam shaft 90. The cam follower roller 120 is thus rotatable about the central axis of the cam shaft 90 and is held in rolling contact with the first cam member 96 on the cam shaft 90. The shaft 116 thus carrying the first arm member 118 on its rear end portion has secured on its front end portion, a second arm member 124 which is also rotatable with the shaft 116 about the center axis of the shaft and which is positioned immediately at the rear of the inclined front wall portion 42c of the upper support member 42. The second arm member 124 on the shaft 116 extends perpendicularly from the front end portion of the shaft 116 in a direction substantially opposite to the direction in which the first arm member 118 extends from the shaft 116. The second arm member 124 has a bifurcated leading end portion 124a located in the vicinity of a toothed rack member 126 projecting upwardly and rearwardly from the previously mentioned front supporting block 48 shown in FIG. 2. The rack member 126 is held in mesh with the spur gear portion 76 of the sleeve member 56 of the instrument receiver unit 52 and is longitudinally movable with respect to the front supporting block 48. The rack member 126 has a pin 128 projecting perpendicularly from an upper end portion of the rack member 126 and is slidably received between the two finger portions constituting the bifurcated leading end portion 124a of the arm member 124. When the cam shaft 90 is driven to turn about the central axis thereof, the first arm member 118 on the shaft 116 is driven for rocking motion about the central axis of the shaft 116 by the rolling contact between the first cam member 96 and the cam follower roller 120 on the arm member 118. Such rocking motion of the first arm member 118 is translated into rocking motion of the second arm member 124 about the central axis of the shaft 116 and are further translated into upward and downward movement of the toothed rack member 126 by pivotal engagement between the bifurcated leading end portion 124a of the second arm member 124 and the pin 128 on the rack member 126. The upward and downward movement of the toothed rack member 126 in turn are converted into rotational motion of the instrument receiver unit 52 by engagement between the toothed rack 126 and the spur gear portion 76 of the sleeve member 56 of the instrument receiver unit 52. The first cam member 96 has a cam surface adapted to ultimately drive the instrument receiver unit 52 to turn from the latched or inoperative angular position to the unlatched or operative angular position and, at a predetermined time interval thereafter, back from the unlatched or operative angular position to the latched inoperative angular position thereof during each full turn of the cam member 96 or accordingly of the gear 112 on the cam shaft 90.

The pledget loading apparatus embodying the present invention further comprises a thrust-out mechanism adapted to forcibly move the probe needle instrument 22 out of the instrument receiver unit 52 conditioned into the unlatched or operative angular position thereof. Such a thrust-out mechanism is also shown principally in FIG. 4 and is designated in its entirety by reference numeral 130.

Figure 7:
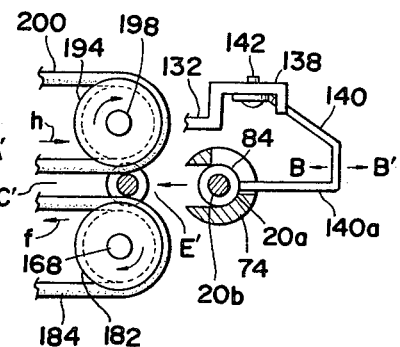
FIG. 7 is a view similar to FIG. 6 but shows the front arrangement of the thurst-out mechanism and the transfer mechanism of the apparatus embodying the present invention.

As shown in FIG. 4, the thrust-out mechanism 130 comprises a slider plate 132 which is slidably received on the upper face of the intermediate wall portion 42b of the upper support member 42. The slider plate 132 has a pin 134 projecting downwardly from the lower face of the slider plate 132 and further downwardly through the previously mentioned elongated slot 46 formed in the inclined intermediate wall portion 42b of the support member 42. The slider plate 132 has rear and front lateral extensions 136 and 138 projecting leftwardly from the remaining major portion of the plate 132. The rear lateral extension 136 of the slider plate 132 is a generally U-shaped cross section and, thus, has a turned-back end portion 136a which is turned back rightwardly or laterally inwardly of the external housing structure 22, viz., in a direction opposite to the direction in which the extension 136 projects from the major portion of the plate 132. The turned-back end portion of the extension 136 has its leading end located and movable in the neighborhood immediately ahead of the rear end portion 78 of the sleeve member 56 of the instrument receiver unit 52 supported by the support member 32 and the supporting block 48, as will be seen from the illustration of FIGS. 1 and 2. On the other hand, the front lateral extension 138 of the slider plate 132 projects generally in parallel with the rear lateral extension 136 from the remaining major portion of the slider plate 132 and has a thrust member 140 secured to the extension 138 by means of a screw 142 as shown in FIG. 7. The thrust member 148 also has a generally U-shaped cross section or overall configuration and has a turned-back end portion 140a which is turned back rightwardly or laterally inwardly of the external housing structure 22, viz., in a direction opposite to the direction in which the front lateral extension projects from the major portion of the slider plate 132. The turned-back end portion 140a of the thrust member 140 has its leading end located and movable in the neighborhood of the quadrant slot 84 in the stem portion 76 of the sleeve member 56 of the instrument receiver unit 52. When the instrument receiver unit 52 is held in the unlatched or operative angular position thereof on the support member 42 and he supporting block 48 as shown in FIG. 7, the turned-back end portion 140a of the thrust member 140 is directed toward the quadrant slot 84 in the sleeve member 56 of the receiver unit 52.

Figure 6:
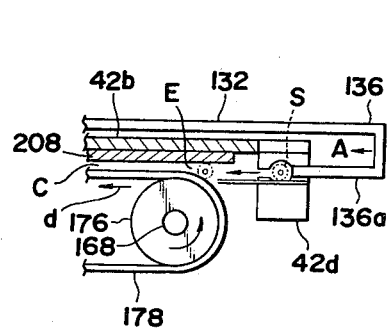
FIG. 6 is a fragmentary rear end view showing part of the rear arrangement including the thrust-out mechanism and the transfer mechanism of the embodiment of the apparatus according to the present invention.

The thrust-out mechanism 130 of the pledge loading apparatus further comprises a cylindrical sleeve member 144 slidably received on a rear axial portion of the previously mentioned shaft 116 of the unlatching mechanism 114, the sleeve member 133 thus being rotatable on the shaft 116 about the central axis of the shaft 116. The sleeve member 144 is positioned rearwardly of the inclined front wall portion 32a of the inner support structure 32 and has fixedly mounted on its intermediate axial portion a first arm portion 146 rotatable with the sleeve portion 144 about the central axis of the shaft 116 and extending perpendicularly from the sleeve 144, as shown in FIG. 4. The first arm member 146 has on its leading end portion a cam follower roller 148 by means of a pin 150 having a central axis substantially parallel with the shaft 116 and accordingly with the cam shaft 90. The cam follower roller 148 is thus rotatable about the axis substantially parallel with the central axis of the cam shaft 90 and is held in rolling contact with the second cam member 98 on the cam shaft 90. The sleeve member 144 thus carrying the first arm member 146 on the intermediate axial portion has at its foremost axial end, a second arm member 152 which is also rotatable with the sleeve member 144 about the center axis of the shaft 116 and which is located above and slightly at the rear of the slider plate 132. The second arm member 152 extends generally downwardly from the sleeve member 144 and has a lower leading end engaged by a link member 154. The link member 154 is partially slidable on the upper face of the slider plate 132 and is pivotally connected adjacent one end thereof to the inclined intermediate wall portion 42b of the upper support member 42 by means of a pivot pin 156 having a central axis normal to the wall portion 42b. The link member 154 has an intermediate longitudinal portion formed with an elongated slot 160 and is further pivotally connected adjacent the other end thereof to the slider plate 132 by means of a connecting pin 158 which is substantially parallel with the pin 156. The connecting pin 158 pivotally connecting the link member 154 to the slider plate 132 projects downwardly through the elongated slot 46 in the inclined intermediate wall portion 42b of the upper support member 42 so that the slider plate 132 is movable back and forth in parallel with the elongated slot 46, viz., rightwardly and leftwardly in the external housing structure 22. The second arm member 152 projecting from the sleeve member 144 on the shaft 116 has its lower leading end movably received in the elongated slot 160 in the link member 154. When thus, the cam shaft 90 is driven to turn about the center axis thereof, the first arm member 146 projecting from the sleeve member 144 is caused to rock about the center axis of the shaft 116 by the rolling contact between the second cam member 98 and the cam follower roller 148 on the arm member 146. Such rocking motion of the first arm member 146 is translated into rocking motion of the second arm member 152 on the sleeve member 144 about the central axis of the shaft 116 and is further translated into rocking motion of the link member 154 about the axis of the pivot pin 156 by engagement between the arm member 152 and the link member 154 through the slot 160 in the link member 154. The rocking motion of the link member 154 in turn is converted into reciprocating movement of the slider plate 132 on the inclined intermediate wall portion 43b of the upper support member 42 by the pivotal connection between the link member 154 and the slider plate 132 through the connecting pin 158. The slider plate 132 being thus moved on the intermediate wall portion 42b of the support member 42 is guided by the pins 134 and 158 projecting from the slider plate 132 into the elongated slot 46 in the wall portion 42b. The slider plate 132 is urged by suitable biasing means to move rightwardly with respect to the upper support 42, viz., in a direction in which the turned-back end portion 136a of the rear lateral extension 136 of the slider plate 132 and the turned-back end portion 140a of the thrust member 140 secured to the front lateral extension 138 of the slider plate 132 are moved laterally inwardly with respect to the external housing structure 22 as indicated by arrows A and B in FIGS. 6 and 7, respectively. In FIG. 4, such biasing means is shown comprising a helical torsion spring 162 which is helically wound on the pivot pin 156 and which is anchored at one end to the link member 154 and the other end to the inclined intermediate wall portion 42b of the support member 42. The torsion spring 162 is, thus, effective not only to urge the slider 132 to move in the above mentioned direction with respect to the upper support member 42 but to urge the cam follower roller 150 against the second cam member 98 through the engagement between the link member 154 and the second arm member 152. The second cam member 98 has a cam surface adapted to ultimately allow the slider plate 132 to move in the above mentioned direction with respect to the support member 42 once during each full turn of the cam member 98 or accordingly of the gear 112 on the cam shaft 90; more exactly, at a predetermined time interval after the instrument receiver unit 52 is caused to turn from the latched or inoperative angular position to the unlatched or operative angular position thereof by the actions of the previously described unlatching mechansim 114. After the slider plate 132 is moved in the particular direction, the slider plate 132 is moved back with respect to the support member 42 by the force of the torsion spring 162. By movement of the slider plate 132 in the reverse direction with respect to the support member 42, the turned-back end portion 136a of the rear lateral extension 136 of the slider plate 132 and the turned-back end portion 140a of the thrust member 140 on the front lateral extension 138 of the slider plate 132 are moved laterally outwardly with respect to the external housing structure 22 as indicated by arrows A' and B' in FIGS. 6 and 7, respectively, In the thrust-out mechanism 130 hereinbefore described, the sleeve member 144 rotatably mounted on the shaft 116 of the unlatching mechanism 114 may be replaced with a shaft (not shown) independent of the shaft 116 and having a central axis fixed with respect to the support structure 32 and substantially parallel with the cam shaft 90. Furthermore, the thrust member 140 is preferably constructed of a metal wire.

The pledget loading apparatus embodying the present invention further comprises an instrument tranfer mechanism for transferring the probe needle instrument 20 from a first or ready-for-transfer position adjacent the leftmost end of the elongated slot 26 in the inclined upper front wall portion 22b of the external housing structure 22, to a second or end-of-transfer position adjacent the rightmost end of the slot 26 in the wall portion 22d of the housing structure 22. Such a transfer mechanism is illustrated principally in FIGS. 8 and 9 of the drawings and is designated generally reference numeral 164 in FIG. 8.

Figure 9:
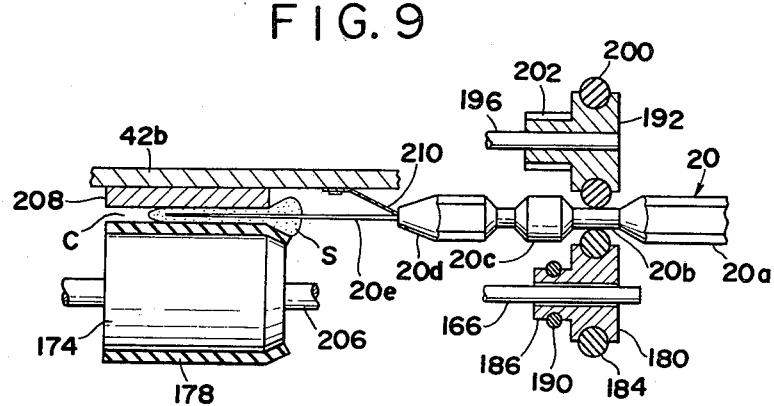
FIG. 9 is a vertical sectional view showing terminal end portions of the transfer mechanism of the apparatus embodying the present invention.
Figure 8:
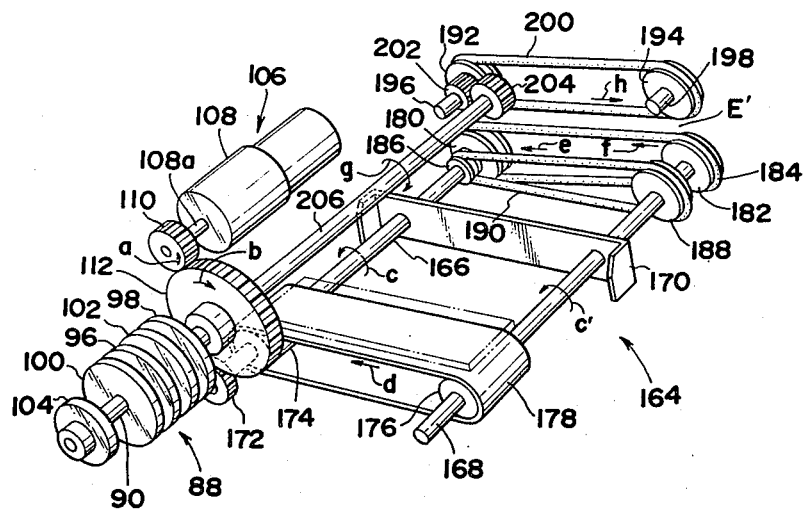
FIG. 8 is a perspective view showing the substantially entire arrangement of the transfer mechanism of the pledget loading apparatus embodying the present invention.

Referring to FIGS. 8 and 9 of the drawings, the instrument transfer mechanism 164 of the apparatus embodying the present invention comprises a pair of spaced parallel shafts consisting of first and second lower transfer shafts 166 and 168 which are spaced apart substantially in parallel from each other in a horizontal direction parallel with the direction in which the elongated slot 26 in the inclined front upper wall portion 22d of the external housing structure 22 extends longitudinally. The transfer shafts 166 and 168 have respective rear end portions rotatably supported by the inclined front wall portion 32a of the internal support structure and respective intermediate axial portions rotatably supported by a cross member 170 secured to the inclined intermediate wall portion 42b of the upper support member 42 and extending perpendicularly to the shafts 166 and 168. Thus, the lower transfer shafts 166 and 168 axially project forwardly and upwardly from the cross member 170 fastened on the intermediate wall portion 42b of the support member 42. One of the lower transfer shafts 166 and 168 such as for example the first lower transfer shaft 166 axially projects rearwardly from the inclined front wall portion 32a of the internal support structure 32 and has fixedly and coaxially mounted on a rear end portion thereof a gear 172 which is held in mesh with the gear 112 on the cam shaft 90. The first lower transfer shaft 166 is thus driven for rotation about the central axis thereof, at a speed proportioned with a fixed ratio to the speed of rotation of the cam shaft 90 when the motor 108 of the drive means 106 is in operation.

The first and second lower transfer shafts 166 and 168 have securely fixed thereon rollers 174 and 176, respectively, which are positioned outside the inclined front wall portion 32a of the internal support structure 32 and which have substantially equal diameters. The rollers 174 and 176 are herein assumed to have substantially equal diameters from the central axes of the transfer shafts 166 and 168, respectively. An endless needle-carrier belt 178 having a considerably large width is passed between the rollers 174 and 76 so that the rotation of the gear meshed with the gear 112 on the cam shaft 90 is carried to the second transfer shaft 168 through the first lower transfer shaft 166, the roller 174 on the shaft 166, the needle-carrier belt 178 and the roller 176 on the second lower transfer shaft 168. In the arrangement herein shown, it is assumed that the motor 108 of the drive means 106 is to operate to drive the gear 110 on the output shaft 108a of the motor 108 for rotation about the center axis of the shaft 108a counter-clockwise in FIG. 8, viz., in a direction indicated by arrow a in FIG. 8. As a consequence, the cam shaft 90 and accordingly the cam members 96, 98, 100, 102 and 104 and the rear 112 on the cam shaft 90 are driven to rotate about the central axis of the cam shaft 90 clockwise in FIG. 8, viz., in a direction indicated by arrow b in connection with the gear 112 in FIG. 8. It therefore follows that the first and second lower transfer shafts 166 and 168 are driven by the gear 172 for rotation about the respective central axes thereof, counter-clockwise in FIG. 8, viz., in directions indicated by arrows c and c', respectively, in FIG. 8. The rotation of the shafts 166 and 168 in the directions of the arrows c and c' causes the needle-carrier belt 178 to travel in directions in which the belt 178 has an upper travelling path portion advancing rightwardly when viewed from the front side of the external housing structure 22, viz., in a direction indicated by arrow d in FIG. 8.

The transfer mechanism 164 shown in FIGS. 8 and 9 of the drawings further comprise first and second main lower pulleys 180 and 182 coaxially rotatable on front end portions of the first and second lower transfer shafts 166 and 168, respectively. A lower main endless belt 184 is passed between these pulleys 180 and 182. The pulleys 180 and 182 being rotatable on the shafts 166 and 168, respectively, and no driving torque is directly transmitted from the shafts 166 and 168 to the pulleys 180 and 182. The transfer mechanism 164 further comprises auxiliary lower pulleys 186 and 188 which are coaxially mounted on the first and second lower transfer shafts 166 and 168, respectively. The first auxiliary lower pulley 186 is secured to the first main lower pulley 180 and is accordingly-rotatable on the first lower transfer shaft 166 about the central axis of the shaft 166. On the other hand, the second auxiliary lower pulley 188 is secured to the second lower transfer shaft 168 and is thus rotatable together with the shaft 168 about the central axis of the shaft 168. An auxiliary lower endless belt 190 is passed between these auxiliary lower pulley 186 and 188. The second auxiliary pulley 188 is rotatable with the second lower transfer shaft 168, the rotation transmitted to the second lower transfer shaft 168 as above described is carried to the first main lower pulley 180 through the second auxiliary lower pulley 188 on the second lower transfer shaft 168, the auxiliary lower endless belt 190, and the first auxiliary lower pulley 186 secured to the first main lower pulley 180. The second lower transfer shaft 168 is driven to rotate about the central axis thereof in the direction indicated by the arrow c' in FIG. 8, the auxiliary lower endless belt 190 is driven to have an upper straight travelling path portion directed as indicated by arrow e and, as consequence, the main lower endless belt 184 is driven to have an upper straight travelling path portion indicated by arrow f in FIG. 8. Thus, the main and auxiliary lower endless belts 184 and 190 are driven to travel in the same directions as the direction in which the endless needlecarrier belt 178 is driven to travel between the shafts 166 and 168. The first and second main lower pulleys 180 and 182 are herein assumed to have substantially equal diameters. The first auxiliary lower pulley 186 is smaller in diameter than these main lower pulleys 180 and 182 and further than the second auxiliary lower pulley 188 which is herein assumed to be substantially equal in diameter to the main lower pulleys 180 and 182. As a consequence, the first auxiliary lower pulley 186 and accordingly, also the first and second main lower pulleys 180 and 182 are driven to rotate with a number of turns larger than the number of turns of the second auxiliary lower pulley 188 and accordingly of each of the first and second lower transfer shafts 166 and 168. Thus, the main lower endless belt 184 is driven to travel between the pulleys 180 and 182 at a speed which is higher at a predetermined ratio, than the speed at which the needle-carrier belt 178 is driven to travel between the rollers 176 and 174. Each of the main and auxiliary lower belts 184 and 190 preferably has a substantially circular cross section as will be seen from FIGS. 8 and 9. As will also be seen from FIG. 9, each of the pulleys 180, 182, 186 and 188 hereinbefore described is preferably of the type which is grooved along its circumference.

The transfer mechanism 164 shown in FIGS. 8 and 9 further comprises first and second upper pulleys 192 and 194 which are coaxially rotatable on first and second upper transfer shafts 196 and 198, respectively. The shafts 196 and 198 are perpendicularly cantilevered at their front ends to the inclined front wall portion 42c of the upper support member 42 and axially project rearwardly and downwardly from the inner or rear face of the wall portion 42c. The first and second upper transfer shafts 196 and 198 thus extend substantially in parallel with and above front end portions of the first and second lower transfer shafts 166 and 168, respectively. An upper endless belt 200 is passed between the upper pulleys 192 and 194. The upper endless belt 200 also preferably has a substantially circular cross section and each of the pulleys 192 and 194 is also preferably of the type which is circumferentially grooved, as will be seen from FIGS. 8 and 9.

While the lower belt and pulley arrangement is driven by the cam shaft 90 through the intermediary of the needle-carrier belt and pulley arrangement, the upper belt and pulley arrangement including the pulleys 192 and 194 and the endless belt 200 as above described, is driven by the cam shaft 90 through belt drive means independent of the needle-carrier belt and pulley arrangement. In FIG. 8, such belt drive arrangement is shown comprising a gear 202 secured to the first upper pulley 192 and coaxially rotatable on the first upper transfer shaft 196, and a gear 204 held in mesh with the gear 202 and coaxially secured to a leading or front end portion of a forward extension 206 of the cam shaft 90. The rotation of the cam shaft 90 about the central axis thereof is thus transmitted to the first upper pulley 192 through the extension 206 of the cam shaft 90, the gear 204 on the extension 206, and the gear 202 secured to the pulley 192. The extension 206 of the cam shaft 90 being rotated about the central axis thereof in a direction indicated by arrow g in FIG. 8, the endless belt 200 passed between the first and second upper pulleys 192 and 194 is driven to travel in a direction to have a lower straight travelling path portion directed as indicated by arrow h in FIG. 8. The direction of travel of the lower straight travelling path portion of the upper endless belt 200 is, thus, opposite to the direction of travel of the upper travelling path portion of the main lower endless belt 184.

The lower transfer shafts 166 and 168 are arranged so that the needle-carrier belt 178 has an upper straight travelling path portion substantially perpendicular to the previously mentioned major frontal plane of the external housing structure 22 and parallel with the lower face of the inclined intermediate wall portion 42b of the upper support member 42 as will be seen from FIGS. 5 and 9. The inclined intermediate wall portion 42b of the support structure 42, has securely attached to its outer or lower face an elongated strip 208 having a frictional outer surface. The elongated strip 208 extends longitudinally along the upper travelling path portion of the needle-carrier belt 178 and has its frictional outer or lower surface spaced apart substantially in parallel from the upper straight travelling path portion of the belt 178 so that a substantially uniform clearance C is formed between the outer or lower surface of the elongated strip 208 and the upper straight travelling path portion of the belt 178. The upper straight travelling path portion of the needle-carrier belt 178 is substantially flush with the plane on which the probe needle 20e of the needle instrument 20 inserted into the previously described instrument receiver unit 52. It is held in a limit rearmost axial position in the receiver unit 52 lies, as will be understood more clearly as the description proceeds. The above mentioned clearance C is sized to be capable of closely receiving therein the probe needle 20e of the needle instrument 20 as will be seen from FIG. 6.

The lower transfer shafts 166 and 168 and the upper transfer shafts 196 and 198 of the transfer mechanism 164 are further arranged so that the upper straight travelling path portion of the main lower endless belt 184 and the lower straight travelling path portion of the upper endless belt 200 have formed therebetween a substantially uniform clearance C' as indicated in FIG. 7. The clearance C' is substantially parallel and aligned with the above mentioned clearance C between the elongated strip 208 and the upper straight travelling path portion of the needle-carrier belt 178 it is sized in such a manner as to be capable of closely receiving therein, the previously mentioned shank portion 20b of the probe needle instrument 20 as will be seen from FIG. 7.

The transfer shafts 166, 168, 196 and 198 of the transfer mechanism 164 are further arranged so that each of the above mentioned clearances C and C' is elongated substantially to correspond with the elongated groove 26 in the inclined upper front wall portion 22d of the external housing structure 22 shown in FIG. 1. Thus, the clearance C between the elongated strip 208 and the needle-carrier belt 178 has an entrance end portion E which is laterally close to an area into which the probe needle 20e of the needle instrument 20, installed into the previously mentioned limit rearmost axial position thereof, in the instrument receiver unit 52, axially extends. Such an area is located at the rear of the downwardly bent lug portion 42d of the upper support structure 42 and is herein referred to as pledget delivery area in which a pledget. For example, absorbent cotton is to be applied to a pointed leading portion of the probe needle 20e of the instrument 20 held in the limit rearmost axial position thereof in the instrument receiver unit 52, as will be described in more detail. Each of the entrance end portions E and E' of the above mentioned clearances C and C', respectively, is substantially aligned or located in substantial correspondence with a left end portion of the elongated slot 26 in the inclined upper front wall portion 22d of the external housing structure 22 shown in FIG. 1.

The above described arrangement of the shafts 166, 168, 196 and 198 of the transfer mechanism 164 is further such, that the clearance C' formed between the respective upper and lower straight travelling path portions of the lower and upper endless belts 184 and 200 has an entrance end portion E', which is laterally close to an area through which the shank portion 20b of the needle instrument 20, installed in the limit rearmost axial position thereof, is in the instrument receiver unit 52, as will be seen from FIG. 7.

Though not shown in the drawings, each of the above mentioned clearances C and C' has an exit end portion which is substantially aligned or located substantially corresponding with a right end portion of the elongated slot 26 in the inclined upper front wall portion 22d of the external housing structure 22 shown in FIG. 1. A suitable guide plate 210 may be securely attached to the outer or lower face of the inclined intermediate wall portion 42b of the upper support member 42 and located to be engageable with the needle holder element 20d of the probe needle instrument 20 located between the respective exit end portions of the clearances C and C' as illustrated in FIG. 9. The guide plate 210 is adapted to guide probe needle instrument 20 to be moved into a position partly located in such exit end portions of the clearances C and C' when the needle instrument 20 is being moved along the elongated slot 26 in the wall portion 22d of the housing structure 22 (FIG. 1) and approaching the right end portion of the slot 26.

The pledget loading apparatus embodying the present invention further comprises a pledget supply mechanism adapted to intermittently feed a pledget of absorbent cotton or any other form of flocculent material to the previously mentioned pledget delivery area. Such a pledget supply mechanism is illustrated principally in FIGS. 10 and 11 of the drawings and is designated generally by reference numeral 212.

Figure 10:
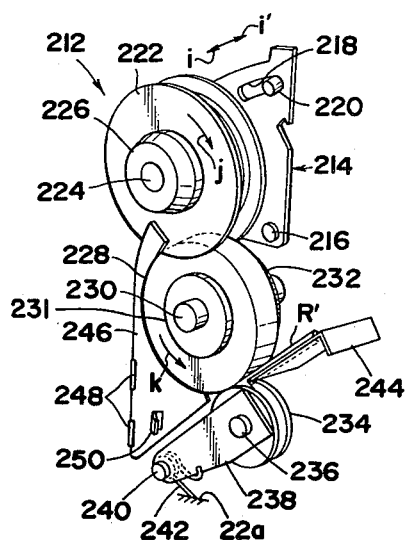
FIG. 10 is a perspective view showing part of the arrangement of the pledget supply mechanism of the embodiment of the pledget loading apparatus according to the present invention.
Figure 11:
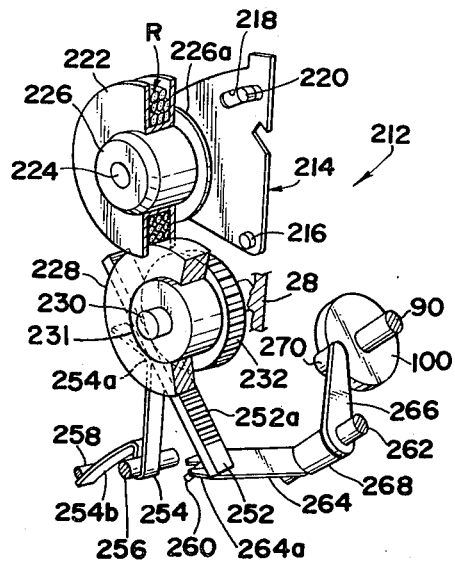
FIG. 11 is a partially cut-away view also showing the arrangement of the pledget supply mechanism of the apparatus embodying the present invention.

As illustrated in FIGS. 10 and 11, the pledget supply mechanism 212 comprises a swivel support plate 214 positioned laterally outside the left internal side member 28 seen in FIG. 1. The swivel support plate 214 is pivotally mounted on the left internal side member 28 by means of a pivot pin 216 having a center axis in a horizontal lateral direction of the external housing structure 22 (FIG. 1) and is thus rotatable in rearward and forward directions indicated by arrows i and i', respectively, about the central axis of the pin 216 with respect to the housing structure 22. The swivel support plate 214 is formed with an arcuate slot 218 into which a pin 220 projects axially, perpendicularly from the outer face of the left internal side member 28. By the engagement of the pin 220 with the swivel support plate 214 through the arcuate slot 218, the swivel support plate 214 is prevented from being turned in the directions of the arrows i and i' beyond predetermined rearmost and foremost angular positions about the central axis of the pivot pin 216. The swivel support plate 214 thus supported by the left internal side member 28 has fixedly mounted thereon a shaft 224 projecting axially, perpendicularly from the outer face of the support plate 214. The shaft 224 coaxially receives thereon, a cylindrical bushing 226 which is circumferentially slidable on the shaft 224. The bushing 226 in turn coaxially receives thereon, a centrally bored spool 222 which has a hollow central drum portion fitted on the outer peripheral surface of the bushing 226. The spool 222 further has a pair of spaced parallel flange portions radially extending from the opposite axial ends of the drum portion of the spool 222. The bushing 226 has at one axial end thereof an annular flange portion 226a located adjacent the outer face of the swivel support plate 214 and is axially held in position on the shaft 224 by means of the flange portion 226a.

The pledget supply mechanism 212 shown in FIGS. 10 and 11 further comprises a feed roller 228 which is positioned below the above described spool 222. The feed roller 228 is carried on a shaft 230 by means of a one-way clutch 231 coaxially intervening between the roller 228 and the shaft 230. The shaft 230 is secured to the above mentioned left internal side member 28 (FIG. 1) and projects axially, perpendicularly from the outer face of the side member 28, thereby extending substantially in parallel with the shaft 224 carrying the spool 222. The one-way clutch 231 is adapted to transmit rotation thereof, to the feed roller 228 when rotated about the central axis of the shaft 230 in a direction indicated by arrow k in FIG. 10 and to idle on the shaft 230 when rotated in the opposite direction about the central axis of the shaft 230. The feed roller 228 is vertically aligned with the spool 222 and has its axial length slightly smaller than the axial spacing between the side flange portions of the spool 222 positioned above the roller 228. The shaft 230 thus carrying thereon the feed roller 228 through the one-way clutch 231, has further rotatably mounted thereon, a ratchet wheel or spur pinion 232 which is coaxially secured to the one-way clutch 231.

A nip roller 234 is positioned below the feed roller 228 being rotatable on a pin 236 secured to and axially projecting from a roller support arm member 238. The roller support arm member has pin 236 located adjacent one end thereof, and is pivotally connected adjacent the other end thereof to a pin 240 secured to the left internal side member 28 and axially projecting perpendicularly from the outer face of the side member 28, as will be seen from FIGS. 1 and 10. Each of the pins 236 and 240 connected to the roller support arm member 238 has a center axis substantially parallel with the shafts 224 and 230 carrying the spool 222 and the feed roller 228, respectively. The nip roller 234 is thus rotatable with respect to the roller support arm member 238 and, furthermore, the roller support arm member 238 is rockable with respect to the internal side member 28 about the axes which are substantially parallel with the axis of rotation of the feed roller 228 and the axis of rotation of the spool 222. The nip roller 234 is upwardly substantially aligned with the feed roller 228 and is constantly pressed against the outer peripheral surface of the feed roller 228 by suitable biasing means. In FIG. 10, such biasing means is shown comprising a helical torsion spring 242 which is helically wound around the pin 240 and which is anchored at one end thereof to the roller support arm member 238 and at the other end thereof to the bottom wall portion 22a of the housing structure 22. The nip roller 234 has a circumferential groove having a semicircular cross section.

The pledget supply mechanism 212 of the apparatus embodying the present invention further comprises an inclined ribbon guide member 244 secured to the outer face of the left internal side member 28, having an upper guide face slanting upwardly and forwardly from the vicinity of the nip between the feed and nip rollers 228 and 234. The pledge mechanism 212 further comprises a vertical ribbon guide plate 246 which is hingedly connected along its rear vertical end to the inner face of the vertical rear wall portion 22f of the external housing structure 22 by means of a suitable number of hinges 248 as shown in FIGS. 1 and 10. The ribbon guide plate 246 is thus pivotally movable about its rear vertical end between a forwardly directed angular position having a portion adjacent the laterally outer faces of the spool 222 and the feed roller 228 as shown and a laterally directed angular position (not shown). Thus, allowing unobstructed access to areas at the rear of the spool 222 and the feed roller 228 from the left side of the spool and feed roller, when the left side wall member 22g of the external housing structure 22 is open as shown in FIG. 1.

The previously described ratched wheel or spur pinion 232 secured to the one-way clutch 231 on the shaft 230 carrying the feed roller 228 thereon, is in mesh with an elongated toothed rack member 252 having lateral teeth 252a engaged by the teeth of the ratchet wheel or spur pinion 232, as shown in FIG. 11. The toothed rack member 252 is held in mesh with the ratchet wheel or spur pinion 232 by suitable biasing means pressing the rack member 252 against the ratchet wheel or spur pinion 232. In FIG. 11, such biasing means is shown comprising a leaf spring 254 having an intermediate portion bent in hairpin form and retained to a spring supporting rod 256 secured to the left internal side member 28 and axially extending substantially in parallel with the shaft 230 carrying the ratchet wheel or spur pinion 232 thereon. The leaf spring 254 further has an upper end portion 254a extending upwardly away from the spring supporting rod 256 and elastically pressed against the rear plain face of the toothed rack member 252. A lower end portion 254b is anchored to a spring retainer rod 258 also secured to the left internal side member 28 and rearwardly spaced substantially in parallel with the spring supporting rod 254 as shown. The toothed rack member 252 longitudinally extends approximately in parallel with the previously mentioned major frontal plane of the external housing structure 22 (FIG. 1) and has a pin 260 projecting rearwardly from a lower end portion thereof.

As illustrated in FIG. 11 and further partially in FIG. 4 of the drawings, the pledget supply mechanism 212 of the apparatus embodying the present invention, further comprises a shaft 262 which has opposite, front and rear end portions respectively secured to the inclined front and rear wall portions 32a and 32b (FIGS. 4 and 5) of the internal support structure 32 and which axially extends substantially in parallel with the cam shaft 90. The shaft 262 has coaxially mounted thereon a hollow sleeve member 268 which is circumferentially slidable on the peripheral surface of an axial portion of the shaft 262. First and second arm members 264 and 266 are connected thereto, extending in approximately opposite directions from the opposite axial ends of the sleeve member 268 and perpendicularly from the central axis of the shaft 262. The first arm member 264 has a bifurcated leading end portion 264a held in engagement with the pin 260 projecting from the 252. The second arm member 266 has a cam follower 252, while the second arm member 266 having a cam follower roller 270 carried on a leading portion of the arm member 266 by means of a pin having a central axis substantially parallel with the shaft 262 and accordingly with the cam shaft 90 as will be seen from FIG. 4. The cam follower roller 270 on the second arm member 266 is thus rotatable about the axis substantially parallel with the cam shaft 90 and is held in rollable contact with the third motion control cam member 100 on the cam shaft 90. As the third motion control cam member 100 is driven to rotate with the cam shaft 90 about the center axis of the cam shaft 90, the cam follower roller 270 is driven to move in an arc toward and away from the central axis of the cam shaft 90 and causes the second arm member 266 and accordingly the first arm member 264 to rock each in opposite directions about the central axis of the shaft 262. The rocking motion of the first arm member 264 about the central axis of the shaft 262 is transmitted to the toothed rack member 252 through the engagement between the bifurcated leading end portion 264a of the arm member 264 and the pin 260 on the toothed rack member 252. Thus, the rocking motion of the arm member 264 are converted into reciprocating motion of the toothed rack member 252. The reciprocating motion of the toothed rack member 252 in turn is converted into oscillating motion of the ratchet wheel or spur pinion 232 about the central axis of the shaft 230 causing the one-way clutch 231 to turn alternately in the opposite directions about the central axis of the shaft 230. When the one-way clutch 231 is caused to turn about the central axis of the shaft 230 in the direction indicated by the arrow k in FIG. 10, the feed roller 228 is driven to rotate with the one-way clutch 231 about the central axis of the shaft 230. During each period of time when the one-way clutch 231 is being rotated about the central axis of the shaft 230 in the direction opposite to the direction of the arrow k, the clutch 231 simply idles on the shaft 230 so that the feed roller 228 stays at rest with respect to the shaft 230. Thus, the feed roller 228 is driven to turn in the direction of the arrow k through a certain angle about the central axis of the shaft 230 in response to each oscillatory motion of the ratchet wheel or spur pinion 232, Viz., to each oscillatory motion of each of the first and second arm members 264 and 266 about the central axis of the shaft 262. The third motion control cam member 100 is adapted to ultimately cause the feed roller 228 to make two intermittent angular motions each through a predetermined angle about the central axis of the shaft 230 in the direction of the arrow k each time the cam member 100 makes a full turn about the central axis of the cam shaft 90.

When the apparatus according to the present invention is in use, a continuous length of flocculent material in the form of, for example, a lengthy ribbon R of absorbent cotton is wound in layers on the drum portion of the spool 222 as indicated in FIG. 11. A leading end portion R' of the ribbon R of the absorbent cotton thus stored on the spool 222 is passed from the spool 222 downwardly and rearwardly from to the feed roller 228; it is further passed partially around the feed roller 228 and between the feed roller 228 and the nip roller 234 to the upper guide face of the inclined ribbon guide plate 244. The swivel support plate 214 and accordingly the spool 222 are biased to turn rearwardly and downwardly about the central axis of the pivot pin 216 by the respective weights thereof and the weight of the ribbon R of the absorbent cotton stored on the spool 222. The spool 222 is for this reason held about the central axis of the pivot pin 216 at an angular position resting on the feed roller 228 through the roll of the ribbon R of the absorbent cotton stored on the spool 222. The intermittent turning motion of the feed roller 228 about the central axis of the shaft 230 as caused by the oscillatory motion of the first and second arm members 264 and 266 on the shaft 262, is therefore transmitted to the spool 222 through the layers of the ribbon R on the spool 222. This causes the spool 222 to turn about the central axis of the shaft 224 in a direction indicated by j in FIG. 10. The oscillatory motion of the feed roller 228 is transmitted not only to the spool 222 but to the nip roller 234 which is held in rollable contact with the feed roller 228 by the force of the spring 242. The nip roller 234 is therefore caused to rotate about the center axis of the pin 236 in a direction opposite to the direction of rotation of the feed roller 228. The leading end portion R' of the ribbon R of the absorbent cotton stored on the spool 222 is thus fed a predetermined length through the feed roller 228 and between the feed and nip rollers 228 and 234 to the inclined ribbon guide plate 244 during each of the two angular motions of the feed roller 228 about the central axis of the shaft 230. During each full turn of the third motion control cam member 100, therefore, the leading end portion R' of the ribbon R of the absorbent cotton stored on the spool 222 is fed two predetermined lengths to the upper guide face of the inclined ribbon guide plate 244 past the nip between the feed roller 228 and the nip roller 234. The leading end portion R' of the ribbon R thus fed to the guide plate 244 is cut into a predetermined length by means of a ribbon cutting mechanism which further forms part of the pledget loading apparatus embodying the present invention.

Figure 12:
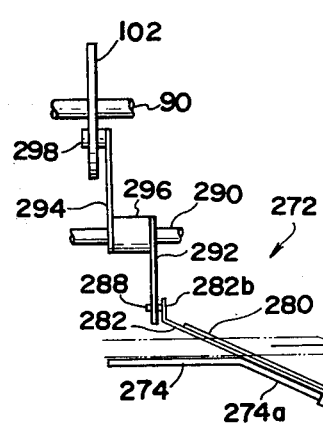
FIG. 12 is a top plan view, somewhat inclined with respect to a horizontal plane, of a ribbon cutting mechanism also forming part of the pledget loading apparatus according to the present invention.
Figure 13:
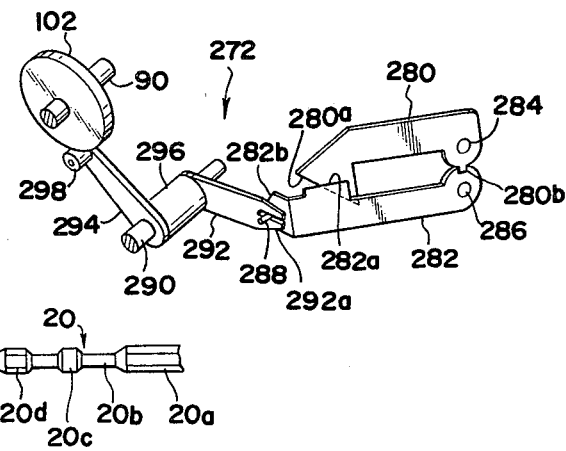
FIG. 13 is a perspective view of the ribbon cutting mechanism illustrated in FIG. 12.

Such a ribbon cutting mechanism is illustrated principally in FIGS. 12 and 13 of the drawings and is designated in its entirety by reference numeral 272. As shown in FIG. 12, the ribbon cutting mechanism 272 comprises a stationary support member 274 which is fixedly connected adjacent its rear end to the shaft 230 supporting the feed roller 228 of the above described pledget supply mechanism 212. The support member 274 is further connected adjacent its front end to the left internal side member 28 by means of a stud or screw 276 as shown in FIG. 1. Furthermore, the support member 274 has a front upper portion 274a laterally inclined outwardly away from the left internal side member 28 as will be seen from FIGS. 1 and 12. An opening 278 is formed in a middle portion of the support member 274 for allowing the turned-back rear lateral extension 136 of the previously described slider plate 132 to laterally move outwardly beyond the support member 274.

On the laterally outwardly inclined front upper portion 274a of the above described support member 274, are mounted two cutting members which consist of first and second or upper and lower cutting members 280 and 282. The upper and lower cutting members 280 and 282 have respective front fulcrum portions pivotally connected to the portion 274a of the support member 274 by pivot pins 284 and 286, respectively, which project perpendicularly from the inner face of the portion 274a as will be seen from FIGS. 12 and 13. The upper cutting member 280 has a rear knife edge portion 280a and the lower cutting member 282 likewise has a knife edge portion 282a which is partially overlapped by and slidable on the knife edge portion 280a of the first cutting member 280. The upper cutting member 280 further has a lug 280b projecting from the fulcrum portion thereof, toward the fulcrum portion of the lower cutting member 282 which, on the other hand, has a recess or notch formed in the fulcrum portion thereof. The lug 280b of the fulcrum portion of the upper cutting member 280 is movably received in the recess or notch in the fulcrum portion of the lower cutting member 282 as will be seen from FIG. 13. Thus, the two cutting members 280 and 282 are caused to pivotally turn concurrently about the central axes of the pivot pins 284 and 286, respectively, when at least one of the cutting members is driven to turn about the central axis of the pivot pin connected thereto. The lower cutting member 282 further has a rear end portion 282b laterally bent away from the support member 274 and has a pin 288 projecting rearwardly from the bent rear end portion 282b.

As shown in FIGS. 12 and 13 and further partially in FIG. 4 of the drawings, the ribbon cutting mechanism 272 further comprises first and second arm members 292 and 294 secured to and extending perpendicularly in approximately opposite directions from the opposite axial end faces of a hollow sleeve member 296, which is coaxially slidable on an axial portion of the shaft 262 carrying the arm members 264 and 266 of the previously described pledget supply mechanism 212. The sleeve member 296 is axially spaced apart from the sleeve member 268 of the pledget supply mechanism 212 by means of a sleeve member 297 mounted on the shaft 262 and axially intervening between the sleeve members 268 and 296, as will be seen from FIG. 4.

The first arm member 292 of the ribbon cutting mechanism 272 has a bifurcated leading end portion 292a having received therein pin 288 projecting from the rear bent portion 282b of the above described lower cutting member 282. On the other hand, the second arm member 294 of the cutting mechanism 272 has a cam follower roller 298 carried on a leading end portion of the arm member 294 by means of a pin with a central axis substantially parallel with the above mentioned shaft 262 and accordingly with the cam shaft 90. The cam follower roller 298 is held in rolling contact with the fourth motion control cam member 102 on the cam shaft 90. The fourth motion control cam member 102 is adapted to drive the cam follower roller 298 to move in an arc away from the central axis of the cam shaft 90 once during each full turn of the cam member 102. By such movement of the cam follower roller 298 away from the central axis of the cam shaft 90, each of the first and second arm members 292 and 294 on the sleeve member 296 is caused to rock about the central axis of the shaft 262 in a counter-clockwise direction in FIG. 13. The rocking motion of the first arm member 292 causes the lower cutting member 282 to turn clockwise in FIG. 13, viz., in a direction to have its knife edge portion 282a moved closer to the knife edge portion 280a of the upper cutting member 280. It therefore follows, that the upper and lower cutting members 280 and 282 are caused to turn toward each other about the center axes of the pivot pins 284 and 286, respectively, by virtue of the engagement of the lug 280b of the cutting member 280 with the fulcrum portion of the cutting member 282. The knife edge portions 280a and 282a of the cutting members 280 and 282, respectively, are thus caused to slide on each other and thereby cooperate with each other to produce a cutting action therebetween. The respective knife edge portions 280a and 282a of the cutting members 280 and 282 are positioned immediately in front of the previously described ribbon guide plate 244 of the pledget supply mechanism 212 and immediately at the rear of the previously mentioned pledge delivery area rearward of the downwardly bent lug portion 42d of the upper support member 42 (FIGS. 2 and 4). The leading end portion R' of the continuous ribbon R fed to the upper guide face of the ribbon guide plate 244 is, thus, cut between the respective knife edge portions 280a and 282a of the cutting members 280 and 282 into the form of a cut segment S of the absorbent cotton as indicated by phantom lines in FIG. 12.

Figure 14:
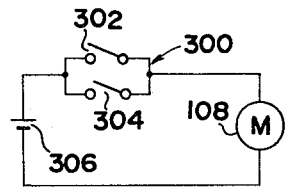
FIG. 14 is a diagram schematically showing the electric circuit arrangement further forming part of the pledget loading apparatus embodying the present invention.

The pledget loading apparatus embodying the present invention further comprises electric switching means for operating the motor 108 of the previously described drive means 106 to start and stop. In FIG. 14 of the drawings, such switching means is generally designated by reference numeral 300 and is diagrammatically shown are comprising first and second switch means 302 and 304. The first and second switch means 302 and 304 are electrically connected in parallel between the motor 108 and a suitable power source such as a d.c. power source 306. The d.c. power source 306 may be constituted by a series of batteries or by an ac-to-dc converter connected to a mains power source through convenience plug and socket (not shown).

Figure 15:
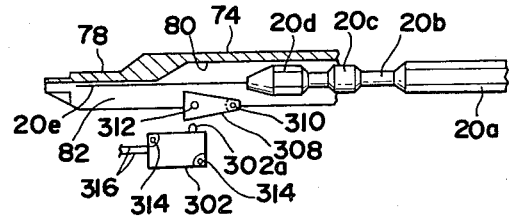
FIG. 15 is a fragmentary side elevation view showing, partially in section, the arrangement including first switch means forming part of the circuit arrangement illustrated in FIG. 14, the first switch means being herein shown in an inoperative or open condition thereof.
Figure 16:
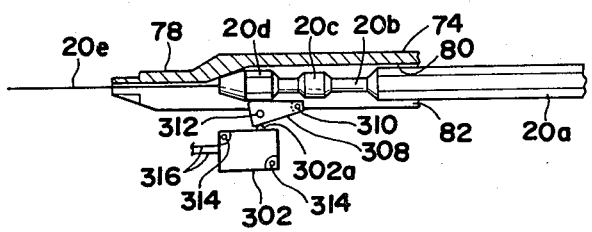
FIG. 16 is a view similar to FIG. 15 but shows the arrangement in which the first switch means illustrated in FIG. 15 is in an operative or closed condition thereof.

The first switch means 302 is adapted to close in response to insertion of the probe needle instrument 20 into the instrument receiver unit 52 and is shown constituted by a normally-closed by a microswitch unit 302 fixedly positioned below the stem portion 74 of the sleeve member 56 of the instrument receiver unit 52 as shown in FIGS. 15 and 16. The microswitch unit 302 has a control plunger 302a axially movable toward and away from the lower end of the stem portion 74 of sleeve member 56 of the instrument receiver unit 52; it is adapted to be open when the control plunger 302a axially projects upwardly toward the stem portion 74 of the sleeve member 56 and to close when the plunger 302a is pressed to axially retract downwardly away from the stem portion 74 of the sleeve member 56. The control plunger 302a of the microswitch unit 302 is urged to axially protrude upwardly by suitable biasing means (not shown) incorporated in the microswitch unit 302 which is accordingly biased to be open. The first switch means shown in FIG. 15 further comprises a generally sector-shaped switch actuating element 308 which is pivotally connected by a pin 310 to an internal wall portion of the stem portion 74 of sleeve member 54 of the instrument receiver unit 52. The pivot pin 310 has a central axis substantially perpendicular in non-intersecting relationship to the central axis of the sleeve member 56 and axially projects into the axial bore 80 in the sleeve member 56 in such a manner as to enable the actuating element 308 to turn about the central axis of the pivot pin 310 toward and away from the central axis of the sleeve member 56 through the radially open end of the axial bore 80 in the sleeve member 56. The switch actuating element 308 is, thus, pivotally movable about the central axis of the pin 310 between a first or inoperative angular position largely retracted into the axial bore 80 in the sleeve member 56 as shown in FIG. 15 and a second or operative angular position partially protruding out of the axial bore 80 in the sleeve member 56 as shown in FIG. 16. The switch actuating element 308 has fixedly mounted thereon a pin 312 which is located a predetermined distance from the pivot pin 310. When the switch actuating element 308 is turned into the above mentioned operative angular position thereof about the center axis of the pivot pin 310, the pin 312 is located out of the axial bore 80 in the sleeve member 56.

When the instrument receiver unit 52 is held in the previously mentioned latched or inoperative angular position about the central axis thereof and has the axial bore 80 radially open at the bottom of the sleeve member 56, the actuating element 308 has its lower edge engaged by the control plunger 302a of the microswitch unit 302 as will be seen from FIGS. 15 and 16. Under these conditions, the switch actuating element 308 is urged to stay in the above mentioned inoperative angular position thereof, about the central axis of the pivot pin 310 by the control plunger 302a, which is urged to axially protrude upwardly by the biasing means incorporated in the microswitch unit 302.

The switch actuating element 308 is, furthermore, located in the axial bore 80 in the sleeve member 56 in such a manner as to be engaged by the needle holder element 20d of probe needle instrument 20, when the probe needle instrument 20 is inserted into the instrument receiver unit 52 and is being axially moved into the previously mentioned rearmost axial position thereof in receiver unit 52. When the switch actuating element 308 is thus engaged by the needle holder element 20d of the probe needle instrument 20 which is held in the latched or inoperative angular position thereof, the actuating element 308 is pressed to turn downwardly into the above mentioned operative angular position about the central axis of the pivot pin 310 on the sleeve member 56. In so doing, the control plunger 302a is pressed downwardly against the force of the biasing means incorporated in the microswitch unit 302. This causes the microswitch unit 302 to close and provides electrical connection between the d.c. power source 306 and the motor 108. The microswitch unit 302 is fixedly mounted on the previously mentioned left internal side member 28 (FIG. 1) by suitable fastening means such as screws 314 and is electrically connected between the motor 108 and the d.c. power source 306 by lead wires 316.

On the other hand, the second switch means 304 diagrammatically shown in FIG. 14 is adapted to operate under the control of the previously mentioned switch control cam member 104 mounted on the rear end portion of the cam shaft 90 as shown in FIG. 4. Referring to FIG. 4, the second switch means 304 is constituted by a microswitch unit 304 positioned in the neighborhood of the switch control cam member 104 and fixedly mounted on the outer or rear face of the inclined rear wall portion 32b of the internal support structure 32 by suitable fastening means such as screws (not shown). The microswitch 304 also has a control plunger 304a which is axially movable in a direction substantially perpendicular in intersecting or non-intersecting relationship, to the central axis of the cam shaft 90 and is urged to project outwardly by suitable biasing means (not shown) incorporated in the microswitch unit 304, which is accordingly biased to be open. The second switch means shown in FIG. 4 further comprises an elongated switch actuating element 318 which is pivotally connected at one end to the microswitch unit 304 and which is pivotally movable about an axis substantially parallel with the central axis of the cam shaft 90. The switch actuating element 318 has at the other end thereof, a cam follower roller 320 positioned by means of a pin having a central axis substantially parallel with the central axis of the cam shaft 90. The switch actuating element 318 is constantly engaged by the control plunger 304a of the microswitch unit 304 and is urged to be held in rollable contact with the switch control cam member 104 by the control plunger 318. The cam follower roller 320 is movable in an arc toward and away from the central axis of the cam shaft 90, about its pivotal axis fixed with respect to the microswitch unit 304 and is moved away from the central axis of the cam shaft 90, once during a single full turn of the cam member 104. The arcuate motions of the cam follower roller 320 toward and away from the central axis of the cam shaft 90 are converted into rocking motion of the switch actuating element 318 about the pivotal axis thereof so that the actuating element 318 is caused to press the control plunger 304a inwardly with respect to the microswitch unit 304, once during a single full turn of the cam member 104. The switch control cam member 104 is adapted to ultimately cause the switch means 304 to close at a predetermined timing and to remain closed for a predetermined period during each full turn of the cam member 104.

Description will be hereinafter made regarding the operation of the pledget loading apparatus embodying the present invention with concurrent reference to FIGS. 1 to 16 of the drawings.

Before the pledget loading apparatus is to be put to use, a lengthy ribbon R, for example, of absorbent cotton is wound in layers on the spool 222 of the pledge supply mechanism 212 shown in FIGS. 10 and 11 and is passed through the feed roller 228 and the nip roller 234, so as to have a leading end portion R' received on the upper guide face of the ribbon guide plate 244 also forming part of the pledget supply mechanism 212. Ahead of such a leading end portion R' of the continuous ribbon R of absorbent cotton, thus extended to the ribbon guide plate 244, is a cut segment of cotton as indicated as S in FIGS. 7 and 12. It is located in the pledget delivery area at the rear of the reduced rear end portion 78 of the sleeve member 56 of the instrument receiver unit 52 (see FIG. 2). The cut segment of cotton S is formed and conveyed into the pledget delivery area during the last operation of the pledget loading apparatus. Furthermore, the instrument receiver unit 52 is held in the latched or inoperative angular position thereof about the central axis and therefore, as the respective axial bores 62 and 80 in the socket and sleeve members 54 and 56 radially open downwardly. Under these conditions, the quadrant slot 84 in stem portion 74 of the sleeve member 56 of the instrument receiver unit 52 is partially opened upwardly and partially rightwardly of the external housing structure 22 when viewed from front of the housing structure 22. Furthermore, the slider plate 132 forming part of the thrust-out mechanism 130 shown in FIG. 4 is held in a limit leftward lateral position with respect to the upper support member 42 by the force of the spring 162.

When, the probe needle instrument 20 is axially inserted into the instrument receiver unit 52 as far as the instrument reaches to the rearmost limit, thereof, the switch actuating element 308 of the first switch means 302 is forced to turn downwardly about the pin 310 by needle holder element 20d of the probe needle instrument 20 advancing through the axial bore 80 in the sleeve member 56 of the receiver unit 52, (see FIG. 16). The switch actuating element 308 is thus caused to press the control plunger 302a of the microswitch unit 302 downwardly and causes the microswitch unit 302 to close and completes the electric circuit between the motor 108 and the d.c. power source 306 (FIG. 14) through the first switch means 302. Under these conditions, the second switch means 304 is kept open.

When the probe needle instrument 20 inserted into the instrument receiver unit 52 reaches the rearmost axial position thereof in the receiver unit 52 as shown in FIG. 16, the pointed probe needle 20e of the instrument 20 is axially thrust into the cut segment of cotton S, preliminarily delivered into the pledget delivery area at the rear of the instrument receiver unit 52.

When the first switch means 302 is thus closed and accordingly the motor 108 is permitted to start operation at time $t_o$, the cam shaft 90 and accordingly the cam members 96, 98, 100, 102 and 104 thereon are driven for rotation about the central axis of the cam shaft 90 through the gear 110 on the output shaft 108a of the motor 108 and the gear 112 on the cam shaft 90. The rotation of the cam shaft 90 is transmitted to the first lower transfer shaft 166 through gear 112 on the cam shaft 90 and; gear 172 on the transfer shaft 166 and thereby causing the needle-carrier belt 178 to travel in the direction represented by the arrow d and the main lower endless belt 184 to travel in the direction represented by the arrow f in FIG. 8. Rotation of the cam shaft 90 is also transmitted to the gear 202 on the first upper transfer shaft 196 and causes the upper endless belt 200 to travel in the direction represented by the arrow h in FIG. 8.

At a predetermined time $t_1$ subsequent to the time $t_o$ at which the first switch means 302 is closed, the first motion control cam member 96 rotating with the cam shaft 90 actuates the unlatching mechanism 114 to operate and drive the toothed rack member 126 for downward movement with respect to the front supporting block 48. This causes the instrument receiver unit 52 to turn from the latched or inoperative angular position into the unlatched or operative angular position about the central axis thereof; this being due to engagement between the rack member 126 and the spur gear portion 76 of the sleeve member 56 of the instrument receiver unit 52. The instrument receiver unit 52 is therefore caused to have its axial bores 62 and 80 radially open rightwardly of the external housing structure 22 when viewed from the front side of the housing structure 22. Furthermore, the quadrant slot 84 in the stem portion 74 of the sleeve member 56 of the instrument receiver unit 52 when turned into the unlatched or operative angular position, is partially opened upwardly and partially toward the turned-back end portion 140a of the thrust member 140 secured to front lateral extension 138 of slider plate 132 forming part of the thrust-out mechanism 130 shown in FIG. 6.

At the same time, when the instrument receiver unit 52 is turned into the unlatched or operative angular position thereof, the switch actuating element 308 carried by receiver unit 52 is disengaged from the control plunger 302a of the microswitch unit 302 and allows the control plunger 302a to axially project upwardly by the force of the biasing means incorporated in the microswitch unit 302. This causes the microswitch unit 302 to open at the time $t_1$. Prior to the time $t_1$, however, the switch control cam member 104 on the cam shaft 90 is turned into an angular position causing the actuating element 318 to turn into the position pressing the associated control plunger 304a of the microswitch unit 304. Thus, the second switch means 304 is caused to close at time $t_2$ before the first switch means 302 is opened at the time $t_1$. After the first swich means 302 is opened at the time $t_1$, the motor 108 driving the cam shaft 90 is in this fashion continually energized from the d.c. power source 306 through second switch means 302.

Immediately after the instrument receiver unit 52 is thus turned into the unlatched or operative angular position, thereof, the second motion control cam member 98 on the rotating cam shaft 90 initiates the thrust-out mechanism 130 into motion at time $t_3$. In the thrust-out mechanism 130 shown in FIG. 4, the slider plate 132 is moved laterally and rightwardly with respect to the upper support member 42 against the force of the spring 162. As a result, the turned-back end portion 136a of the rear lateral extension 136 of the slider plate 132 is laterally moved toward the probe needle 22e of probe needle instrument 20 projecting axially and rearwardly from the reduced rear end portion 78 of the sleeve member 56 of the receiver unit 56 as will be seen from FIG. 6. On the other hand, the turned-back end portion of thrust member 140 secured to front lateral extension 138 of the slider plate 132 is laterally moved into the quadrant slot 84 in the stem portion 74 of the sleeve member 56 of the instrument receiver unit 52 as will be seen from FIG. 7. As the slider plate 132 is moved rightwardly with respect to the support member 42, the turned-back end portion 136a of rear lateral extensions 136 of the slider plate 132 and the turned-back end portion 140a of thrust member 140 secured to the front lateral extension 138 of the slider plate 132 are brought into laterally pressing contact with the probe needle 20e and the grip rod portion 20a, respectively, of the probe needle instrument 20. Thereby, the needle instrument 20 is thrust out of the axial bores 62 and 80 in the instrument receiver unit 52 and into a position having the needle 20e located in the entrance end portion E (FIG. 6) of the clearance C between needle-carrier belt 178 and the previously described elongated strip 208. The shank portion 20b of the needle instrument 20 being located in the entrance end portion E' (FIG. 7) between the main lower endless belt 184 and the upper endless belt 200 shown in FIGS. 8 and 9. Under these conditions, the grip rod portion 20a of probe needle instrument 20 is withdrawn out of the radial groove 64 in the socket member 54 of the instrument receiver unit 52 and is admitted into the elongated slot 26 in the inclined front upper wall portion 22d of the external housing structure 22.

At time $t_4$ after the probe needle instrument 20 has thus been withdrawn from the instrument receiver unit 52, the second motion control cam member 98 approaches the central axis of the cam shaft 90 at an angular position allowing the slider plate 132 to move laterally back into the initial position thereof with respect to the upper support plate 42 by the force of the spring 162. Subsequently to the backward movement of the slider plate 132, the first motion control cam member 96 is turned at time $t_5$ into an angular position causing the toothed rack member 126 to move upwadly with respect to the front supporting block 48 and thereby causes the instrument receiver unit 52 to resume the latched or inoperative angular position about the central axis thereof.

Now, the probe needle instrument 20 is moved into the position having the probe needle 20e closely received between the lower frictional surface of the elongated strip 208 and the upper travelling portion of the needle-carrier belt 178. The shaft portion 20b is closely received between the upper travelling portion of the main lower endless belt 184 and the lower travelling portion of the upper endless belt 200. Thus, the probe needle 20e and the shank portion 20b of the needle instrument 20 are driven to roll in the laterally elongated clearances C and C', respectively, so that the needle instrument 20 as a whole is conveyed along the elongated slot 26 in wall portion 22d of the external housing structure 22 from the leftmost end portion of the slot 26 toward the rightmost end portion of the slot 26 when viewed from the front side of the housing structure 22.

The shank portion 20b of the probe needle instrument 20 is larger in diameter than probe needle 20e of the instrument 20. The main lower endless belt 184 is for this reason driven to travel faster than the needle-carrier belt 178, as previously described in detail, so that the shank portion 20b and the needle 20e of the instrument 20 are moved on the belts 184 and 178, respectively, at substantially equal speeds. Furthermore, the upper endless belt 200 having the lower travelling portion contacted by the shank portion 20b of the needle instrument 20 is driven to travel in the opposite direction to the direction of travel of the main lower endless belt 184 and thereby aids in rolling motion of the shank portion 20b of the needle instrument 20 being conveyed by the belts 178 and 184.

When the probe needle instrument 20 thus conveyed by the belts 178, 184 and 200 along the elongated slot 26 in the wall portion 22d of the external housing structure 22 reaches the rightmost end portion of the slot 26, the probe needle 20e and shank portion 20b of the needle instrument 20 are withdrawn from the clearances C and C', respectively, past the respective exit end portions of the clearances. The probe needle instrument 20 is now held at rest at the rightmost end of the slot 26 by means of the previously mentioned guide plate 210 (FIG. 9) and, and it is ready to be removed from the pledget loading apparatus with the cut segment of cotton S applied to the probe needle 20e of the instrument 20 as shown in FIG. 9.

After the time $t_4$ when probe needle instrument 20 has been thrust out of the instrument receiver unit 52 as previously described, the third motion control cam member 100 on the cam shaft 90 reaches at time $t_6$; such an angular position about the center axis of the cam shaft 90 is effective to initiate the pledget supply mechanism 212 (FIGS. 10 and 11) into action. The ratchet wheel or spur pinion 232 of the pledget supply mechanism 212 shown in FIGS. 10 and 11. It is thus caused to make a first oscillatory motion starting at the time $t_6$ and thereafter a second oscillatory motion starting at time $t_7$ about the central axis of the shaft 230 and thereby causes the ribbon R of the absorbent cotton to be stepwise unwound from the spool 222 and stepwise passed through the feed roller 228 and the nip roller 234 to the ribbon guide plate 244 of the pledget supply mechanism 212. At a predetermined time interval after the leading end portion R' of the ribbon R of the absorbent cotton is guided to extend forwardly from guide plate 244 into the pledget delivery area at rear of the instrument receiver unit 52, the fourth motion control cam member 102 on the cam shaft 90 is turned about the central axis of the cam shaft 90 at an angular position. This causes the ribbon cutting mechanism 272 to start operation at time $t_8$. The upper and lower cutting members 280 and 282 of the cutting mechanism 272 shown in FIGS. 12 and 13 are now caused to turn about the central axes of the pivot pins 284 and 286, respectively, and cut the leading end portion R' of the cotton ribbon R between their respective knife edge portions 280a and 280b. The leading end portion R' of the cotton ribbon R is now cut from the immediately trailing portion of ribbon R, so as to form a new cut segment of cotton S in the pledget delivery area in front of the pledget guide plate 244.

Upon completion of the operation of the cutting mechanism 272, the switch control cam member 104 on the cam shaft 90 is turned at an angular position allowing the switch actuating element 308 of the second switch means 304 to turn back into the initial angular position thereof by the force of the biasing means incorporated in the microswitch unit 302. The second switch means 304 in the arrangement shown in FIG. 14 is now opened as the first switch means was opened previously, and motor 108 is electrically disconnected from the d.c. power source 306 and is accordingly de-energized. The cam shaft 90 and accordingly the transfer mechanism 164 shown in FIG. 8 are now rendered inoperative so that the pledget loading apparatus terminates its operation and is ready for a subsequent operation.

What is claimed is:

1. An apparatus for applying a cut segment of a flocculent material to an elongated needle instrument having a needle, comprising, in combination, an instrument receiver unit for receiving therein at least an axial portion of said needle instrument in such a manner that the needle of the instrument axially projects out of the receiver unit, said instrument receiver unit having an axial bore extending and laterally open throughout the length of the unit, thrust-out means operative to thrust the needle instrument laterally out of the axial bore in said instrument receiver unit into a predetermined first position laterally adjacent the receiver unit, transfer means operative to convey the needle instrument from said first position to a predetermined second position remote from the first position, supply means for storing a continuous length of flocculent material thereon and feeding a leading end portion of the continuous length of flocculent material to a predetermined delivery area into which the needle of said instrument is to axially extend when the instrument is received in said instrument receiver unit, and cutting means operative to cut said leading end portion into a segment in said delivery area.

2. An apparatus as set forth in claim 1, in which said instrument receiver unit is shiftable between a latched position in which said thrust-out means is inaccessible into said axial bore and an unlatched position in which the thrust-out means is accessible into said axial bore.

3. An apparatus as set forth in claim 2, further comprising unlatching means operative to shift said instrument receiver unit between said latched position and said unlatched position thereof.

4. An apparatus as set forth in claim 3, in which said instrument receiver unit is angularly movable about a predetermined axis between said latched position and said unlatched position thereof, said axial bore in said instrument receiver unit being laterally open away from said axis in a first direction deviating from said first position and a second direction directed toward said first position.

5. An apparatus as set forth in claim 4, in which said unlatching means comprises an externally toothed gear having a center axis substantially coincident with said axis about which said instrument receiver unit is angularly movable.

6. An apparatus as set forth in any of claims 1 to 5, in which said needle instrument has a shank portion larger in diameter than said needle and in which said transfer means comprises an endless needle-carrier belt having a substantially straight travelling path portion extending in a direction substantially parallel with the spacing between said first position and said second position, said needle-carrier belt being adapted to have said needle rollably received thereon along said travelling path portion and a belt and pulley arrangement including an endless belt having a substantially straight travelling path portion substantially parallel with said travelling path portion of said needle-carrier belt, said endless belt of said belt and pulley arrangement being adapted to have said shank portion rollably received thereon along said travelling path portion thereof.

7. An apparatus as set forth in claim 6, in which said endless belt of said belt and pulley arrangement constitutes a first endless belt of the arrangement which further comprises a second endless belt having a substantially straight travelling path portion substantially parallel with said travelling path portion of said first endless belt, said travelling path portion of the first endless belt and said travelling path portion of the second endless belt being spaced apart from each other and having formed therebetween an elongated clearance for receiving therein the shank portion of said instrument.

8. An apparatus as set forth in claim 7, in which said transfer means further comprises drive means operative to drive said needle-carrier belt to travel at a first speed and in a first direction along said travelling path portion thereof, said first endless belt to travel at a second speed and in a second direction identical and parallel with said first direction and said second endless belt to travel at a third speed lower than said first speed and in a direction opposite to and parallel with said first direction.

9. An apparatus as set forth in any of claims 1 to 5, in which said supply means comprises a support member pivotally movable about a fixed horizontal axis, a spool rotatable about an axis fixed with respect to said support member and substantially parallel with the axis about which the support member is pivotally movable, said spool being adapted to have said continuous length of flocculent material wound in layers thereon, a feed roller rotatable about an axis substantially parallel with the axis of rotation of said spool, said spool being radially aligned with said feed roller and being adapted to bear in rollable and weight-transmitting relationship on the feed roller, a nip roller rotatable about an axis substantially parallel with the axis of rotation of said feed roller, and biasing means urging said nip roller into rollable contact with said feed roller.

* * * * *